United States Patent [19]

Martel et al.

[11] 4,061,729
[45] Dec. 6, 1977

[54] PROSTANOIC ACID DERIVATIVES AND THERAPEUTIC COMPOSITIONS

[75] Inventors: Jacques Martel, Bondy; Jean Buendia, Nogent-sur-Marne; Michel Vivat, Lagny-sur-Marne, all of France

[73] Assignee: Roussel Uclaf, Paris, France

[21] Appl. No.: 587,558

[22] Filed: June 17, 1975

Related U.S. Application Data

[63] Continuation-in-part of Ser. No. 425,794, Dec. 18, 1973.

[30] Foreign Application Priority Data

June 21, 1974 France .............................. 74.21602
Dec. 27, 1972 France .............................. 72.46324

[51] Int. Cl.² .................. C07C 177/00; A61K 31/19; A61K 31/215
[52] U.S. Cl. .............................. 424/305; 260/410.9 R; 260/413; 260/514 D; 424/317; 560/121
[58] Field of Search ............... 260/408, 514; 424/305, 424/317

[56] References Cited

U.S. PATENT DOCUMENTS 3,922,302  11/1975  Strike ..................... 260/514

Primary Examiner—Robert Gerstl
Attorney, Agent, or Firm—Hammond & Littell

[57] ABSTRACT

Novel prostanoic acid derivatives of the formula

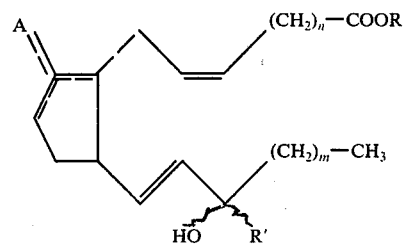

wherein R is hydrogen or alkyl having 1 to 4 carbon atoms, $m$ is a whole number from 3, 4 or 5, $n$ is a whole number from 2, 3 or 4, R' is either a linear or branched, saturated or unsaturated aliphatic hydrocarbon having 1 to 4 carbon atoms, or a saturated or mono unsaturated cyclohydrocarbon having 3 to 6 carbon atoms and A is either alkoxy having 1 to 4 carbon atoms or oxygen of a ketonic group, the dotted lines in the pentagonal ring are possible positions of a single double bond where, when A is a ketonic oxygen, the double bond is on the exterior of the ring and when A is alkoxy, the double bond is in one of the two interior positions of the ring, as well as the pharmaceutically compatible salts of mineral or organic bases when R is hydrogen in their $\alpha,\beta$ or $\beta,\alpha$ forms and mixtures thereof; as well as the process for their preparation, and the therapeutic compositions containing them.

9 Claims, No Drawings

PROSTANOIC ACID DERIVATIVES AND THERAPEUTIC COMPOSITIONS

PRIOR APPLICATION

This application is a continuation-in-part of application Ser. No. 425,794 filed Dec. 18, 1973.

BACKGROUND OF THE INVENTION

The natural products of the family of the prostaglandines, extracts originating from seminal liquids, are undergoing an increasing pharmacological interest and have given rise to various therapeutic trial procedures. However, it has been said that these products have on the one hand, diverse activities of important secondary effects in the treatment of a given application, and on the other hand, a very brief duration of action, which limits their possibility of use.

It has been therefore of interest to synthesis products which would present a disassociation of activities and which would manifest an increased duration of action.

OBJECTS OF THE INVENTION

An object of the present invention is the development of novel prostanoic acid derivatives which, as compared to natural prostaglandines, would have a disassociation of properties and/or a longer duration of the desired activity.

Another object of the present invention is the development of a prostanoic acid derivative having the formula

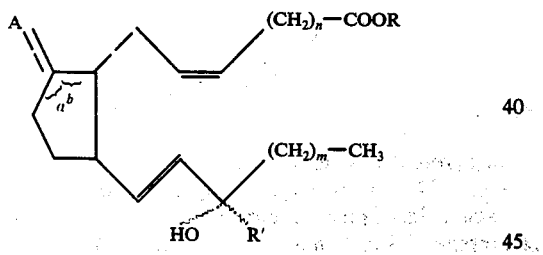

wherein R is a member selected from the group consisting of H, lower alkyl having 1 to 4 carbon atoms and acid salts of pharmaceutically compatible bases, $m$ is an integer 3,4 or 5, $n$ is an integer 2,3 or 4, R' is a member selected from the group consisting of alkyl having 1 to 4 carbon atoms, alkenyl having 2 to 4 carbon atoms, alkynyl having 2 to 4 carbon atoms, cycloalkyl having 3 to 6 carbon atoms and cycloalkenyl having 3 to 6 carbon atoms, A is a member selected from the group consisting of ketonic oxygen and alkoxy having 1 to 4 carbon atoms, one of a or b being a double bond when A is alkoxy, the dotted line to A being a double bond when A is a ketonic oxygen, and the wavy lines represents a paired configuration selected from the group consisting of $\alpha,\beta$ and $\beta,\alpha$ and mixtures thereof.

A further object of the present invention is the development of a process for the preparation of the above prostanoic acid derivative consisting essentially of the steps of 1. subjecting a compound having the formula

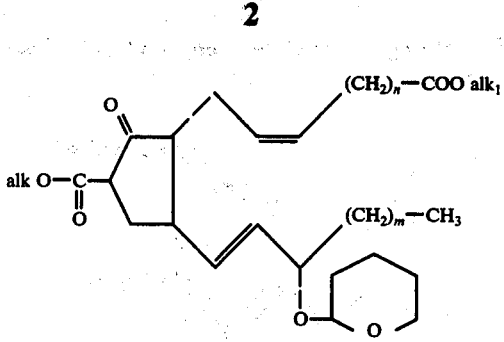

wherein $m$ is an integer 3,4 or 5, $n$ is an integer 2,3 or 4, alk and alk$_1$ represent alkyl having 1 to 4 carbon atoms, to an acid hydrolysis, 2. reacting the resulting compound having the formula

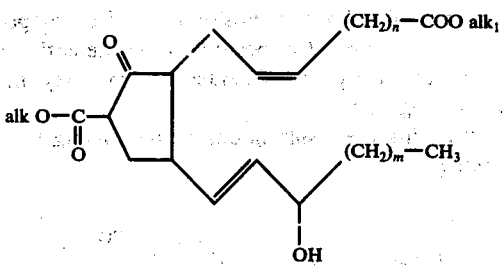

wherein $m$, $n$, alk and alk$_1$ have the above-assigned values, with a diazoalkane having 1 to 4 carbon atoms under alkylation conditions, 3. saponifying the resulting compound having the formula

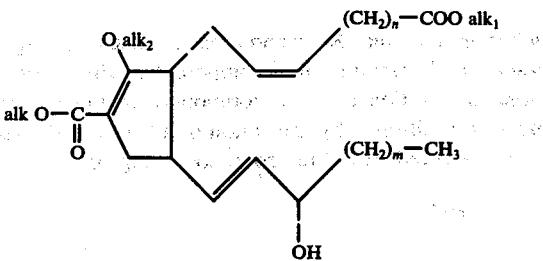

wherein $m,n$, alk and alk$_1$ have the above-assigned values and alk$_2$ represents alkyl having 1 to 4 carbon atoms, by the action of an alkaline base, and acidifying the resultant salt, 4. decarboxylating the resulting acid having the formula

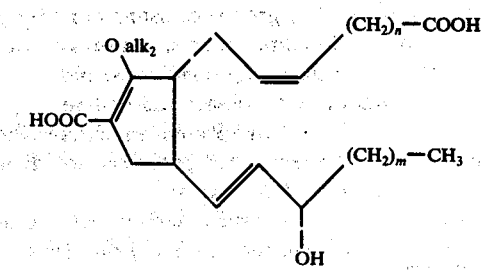

wherein $m,n$ and alk$_2$ have the above-assigned values, by the action of heat, and optionally alkylating with a diazoalkane having 1 to 4 carbon atoms, 5. oxidizing the resulting compound having the formula

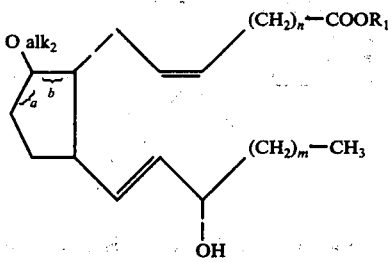

wherein m,n and alk₂ have the above-assigned values, R₁ is a member selected from the group consisting of hydrogen and alkyl having 1 to 4 carbon atoms, and one of a or b is a double bond, and mixtures of a compound having a double bond in position a and a compound having a double bond in position b, by the action of a oxidizing agent capable of oxidizing a hydroxyl group to a ketone group, 6. alkylating the resulting compound having the formula

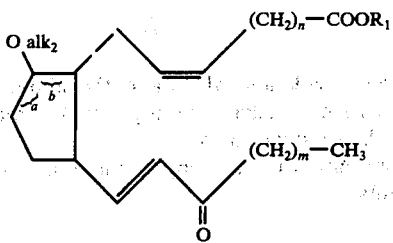

wherein n,m, alk₂, R₁, a and b have the above-assigned values and mixtures of a compound having a double bond in position a and a compound having a double bond in position b, by the action of a ketonic alkylating agent selected from the group consisting of R' MgX and

R''—C≡C—M wherein R' is a member selected from the group consisting of alkyl having 1 to 4 carbon atoms, alkenyl having 2 to 4 carbon atoms, alkynyl having 2 to 4 carbon atoms, cycloalkyl having 3 to 6 carbon atoms and cycloalkenyl having 3 to 6 carbon atoms, X is a halogen, R'' is a member selected from the group consisting of hydrogen and alkyl having 1 to 2 carbon atoms, and M is an alkali metal, under ketonic alkylating conditions, and 7. recovering said prostanoic acid derivatives.

A yet further object of the present invention is the development of therapeutic compositions containing the above prostanoic acid derivatives.

These and other objects of the invention will become more apparent as the description thereof proceeds.

DESCRIPTION OF THE INVENTION

The present invention relates to novel derivatives of the prostanoic acid of formula I

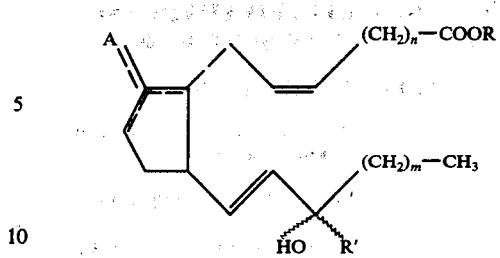

wherein R is hydrogen or alkyl having 1 to 4 carbon atoms m is a whole number from 3,4 or 5, n is a whole number from 2,3 or 4, R' is either a linear or branched, saturated or unsaturated aliphatic hydrocarbon having 1 to 4 carbon atoms, or a saturated or mono unsaturated cyclohydrocarbon having 3 to 6 carbon atoms and A is either alkoxy having 1 to 4 carbon atoms or oxygen of a ketonic group, the dotted lines in the pentagonal ring are possible positions of a single double bond where, when A is a ketonic oxygen, the double bond is on the exterior of the ring and when A is alkoxy, the double bond is in one of the two interior positions of the ring, as well as the pharmaceutically compatible salts of mineral or organic bases when R is hydrogen. The compounds may be in the form of α,β or β,α in the 15-position or mixtures thereof.

More particularly the present invention relates to a prostanoic acid derivative having the formula

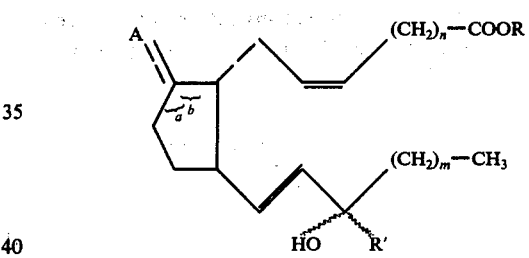

wherein R is a member selected from the group consisting of H, lower alkyl having 1 to 4 carbon atoms and acid salts of pharmaceutically compatible bases, m is an integer 3,4 or 5, n is an integer 2,3 or 4, R' is a member selected from the group consisting of alkyl having 1 to 4 carbon atoms, alkenyl having 2 to 4 carbon atoms, alkynyl having 2 to 4 carbon atoms, cycloalkyl having 3 to 6 carbon atoms and cycloalkenyl having 3 to 6 carbon atoms, A is a member selected from the group consisting of ketonic oxygen and alkoxy having 1 to 4 carbon atoms, one of a or b being a double bond when A is alkoxy, the dotted line to A being a double bond when A is a ketonic oxygen, and the wavy lines represents a paired configuration selected from the group consisting of α,β and β,α and mixtures thereof.

Among the substituents A, where the same is alkoxy, are particularly methoxy and ethoxy. Among the substituents R, where the same is alkyl, are particularly methyl, ethyl, propyl, butyl and tertiary butyl. Among the substituents R' are particularly alkyl such as methyl, ethyl, propyl, isopropyl, butyl and tertiary butyl, alkenyl such as vinyl and butenyl, alkynyl such as ethynyl and propargyl, cycloalkyl such as cyclohexyl, and cycloalkenyl such as cyclohexenyl.

Among the salts of pharmaceutically compatible bases which can form the products of formula I when R represents hydrogen are, for example, the mineral salts, preferably the alkali metal salts such as lithium, sodium or potassium, the alkaline earth metal salts such as calcium, the magnesium salt and the ammonium salt, and the organic salts formed with organic amine bases, such as alkylamines and alkylolamines.

Among the products of formula I, the invention most particularly relates to the prostanoic acids of formula I'

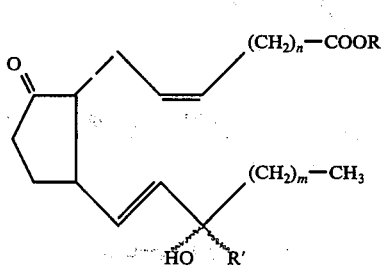

(I)

where R, n, m and R' have the above-assigned values and notably methyl (8RS, 12RS, 15RS)-(5Z, 13E)-15-ethynyl-15-hydroxy-9-oxo-5,13-prostadienoate, methyl (8RS, 12RS, 15SR)-(5Z, 13E)-15-ethynyl-15-hydroxy-9-oxo-5,13-prostadienoate, methyl (8RS, 12RS, 15ξ)-(5Z, 13E)-15-hydroxy-15-methyl-9-oxo-5,13-prostadienoate, and methyl (8RS, 12RS, 15ξ)-(5Z, 13E)-15-hydroxy-15-vinyl-9-oxo-5,13-prostadienoate.

The symbol ξ used in the preceding compound names, as well as the wavy line used in the formulas, signifies here and hereafter, that the substituents attached to the carbon atom thus designated can be found in the two possible configurations about this atom. The corresponding products can thus be mixtures which can be separated into each of the constituents by using customary physical methods, such as chromatographic separation.

The products corresponding to formula I as well as their therapeutically compatible salts can be employed as medicaments. The invention therefore also includes pharmaceutical compositions which contain these substances as the active principle.

The natural products of the family of the prostaglandines, extracts originating from seminal liquids, are undergoing an increasing pharmacological interest and having given rise to various therapeutic trial procedures. However, it has been said that these products have on the one hand, diverse activities of important secondary effects in the treatment of a given application, and on the other hand, a very brief duration of action, which limits their possibility of use.

It has been therefore of interest to synthesis products which would present a disassociation of activities and which would manifest an increased duration of action.

The products of the invention present such disassociation of activities and/or increased duration of action. The products of formula I manifest in pharmacology a hypotensive activity, a contracturant activity on the smooth muscles and an antibronchoconstrictive activity.

In particular, the hypotensive activity of these products was found to be, in most respects at some or all dosage levels, more long lasting than the hypotensive activity of the natural prostaglandines. The pharmacological results obtained with these products are set out hereafter.

The pharmacological properties of the products of the invention are such that they are utilizable as medicaments particularly in the treatment of hypertension and circulatory disturbances as well as in the treatment of respiratory afflictions such as asthma for example.

The products can be administered to warm-blooded animals parenterally, orally, rectally or locally by topical application to the skin or mucous membranes.

The pharmaceutical preparations can be presented in the form of injectable solutions or suspensions, sterile powders for preparation of extemporaneous injections, simple or coated tablets, capsules, syrups, suppositories, creams, pomades and aerosol preparations. These pharmaceutical forms are prepared according to the classic processes of pharmacotechnology.

The dose administered is varied according to the affliction being treated, the patient, the method of administration and the product being administered. It can range for example, from 0,2 μg/kg to 0,02 mg/kg in the warm-blooded animal depending on the above. It can be, for example, between 10 μg and 1 mg for methyl (8RS, 12RS, 15SR)-(5Z, 13E)-15-ethynyl-15-hydroxy-9-oxo-5,13-prostadienoate, when administered by an injectable method, for example, by slow perfusion in man. When administered as an aerosol, the dosage could be on the order of from 50 to 500 μg.

The invention equally concerns the process for the preparation of the products of formula I which is characterized in the steps of:

1. subjecting a compound having the formula II

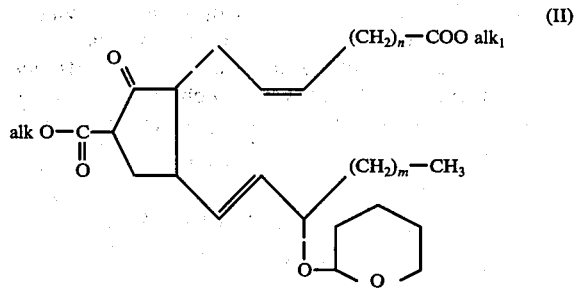

(II)

wherein m is an integer 3, 4 or 5, n is an integer 2, 3 or 4, alk and alk$_1$ each represent a similar or different alkyl having 1 to 4 carbon atoms, to an acid hydrolysis, 2. reacting the resulting compound having the formula III

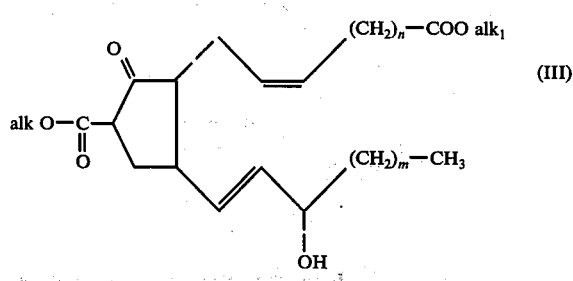

(III)

wherein m, n, alk and alk$_1$ have the above-assigned values, with a diazoalkane having 1 to 4 carbon atoms under alkylation conditions, 3. saponifying the resulting compound having the formula IV

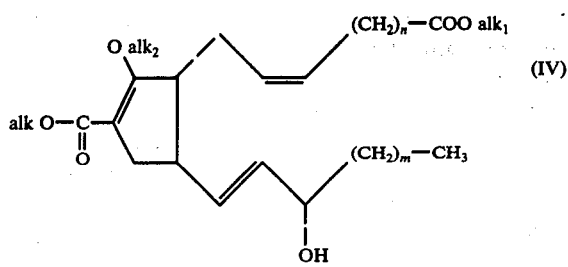

(IV)

wherein *m*, *n*, alk and $alk_1$ have the above-assigned values and $alk_2$ represents alkyl having 1 to 4 carbon atoms, by the action of an alkaline base, and acidifying the resultant salt, 4. decarboxylating the resulting acid having the formula V

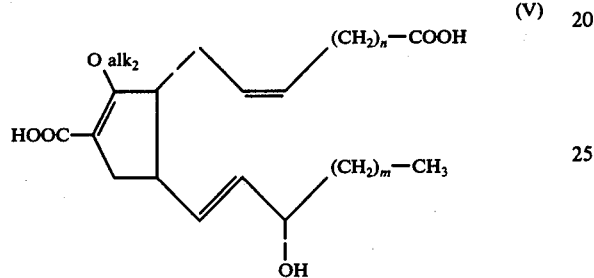

(V)

wherein *m*, *n* and $alk_2$ have the above-assigned values, by the action of heat in order to cause a decarboxylation on the cyclopentanoic ring, and optionally alkylating with a diazoalkane having 1 to 4 carbon atoms, 5. oxidizing the resulting mixture of compounds having formulas VI and VI', which mixture can be separated into each of its constituents, or one of its constituents,

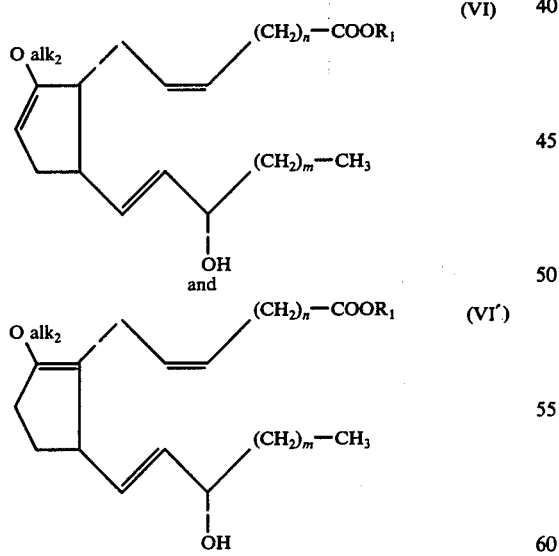

(VI)

and (VI')

wherein *m*, *n* and $alk_2$ have the above-assigned values, $R_1$ is a member selected from the group consisting of hydrogen and alkyl having 1 to 4 carbon atoms, by the action of a oxidizing agent capable of oxidizing a hydroxyl group to a ketone group, 6. alkylating the resulting mixture of compounds, or one of them, having the formulas VII and VII'

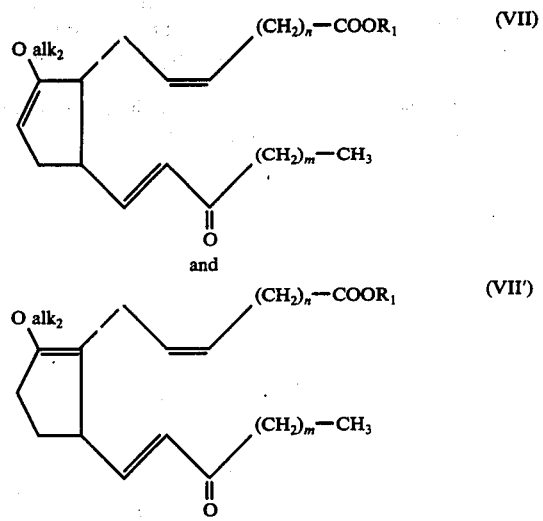

(VII)

and (VII')

wherein *n*, *m*, $alk_2$, and $R_1$ have the above-assigned values, by the action of a ketonic alkylating organomagnesium agent of the formula $$R' Mg X$$

wherein R' is a member selected from the group consisting of alkyl having 1 to 4 carbon atoms, alkenyl having 2 to 4 carbon atoms, alkynyl having 2 to 4 carbon atoms, cycloalkyl having 3 to 6 carbon atoms and cycloalkenyl having 3 to 6 carbon atoms, X is a halogen, and 7. recovering a mixture of products having the formulas

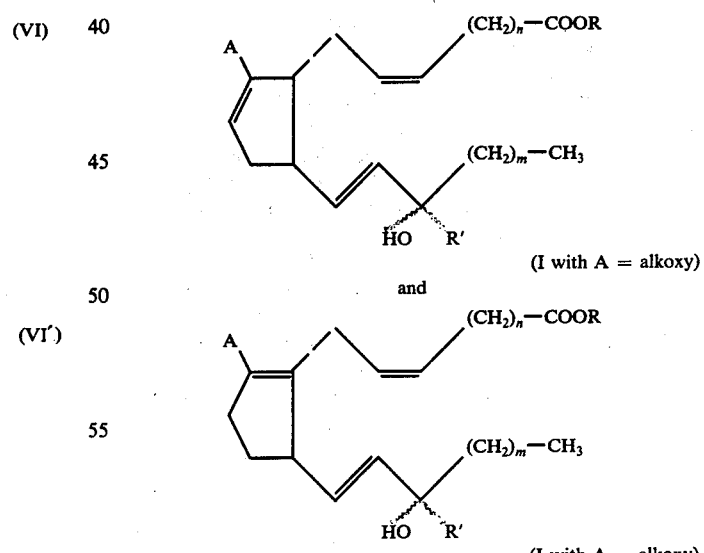

(I with A = alkoxy)

and (I with A = alkoxy)

which, if desired, can be separated into its constituents, which can be neutralized, if desired, by the usual methods when R=H, or, if desired, the preceding mixture of products of formula I or one of its constituents can be treated with an acid in order to obtain a mixture or one of the products having the formula

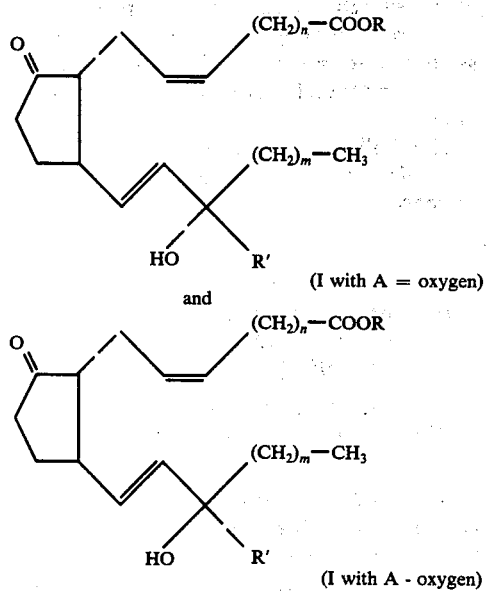

(I with A = oxygen)

and (I with A - oxygen)

The passage of products of the formula II to products of the formula III is made with the aid of an acid in an aqueous media at temperatures up to the boiling point, preferably in the presence of a water-miscible organic solvent. Preferably oxalic acid is utilized, but other organic acids soluble in water such as formic acid or acetic acid, or mineral acids such as hydrochloric acid or sulfuric acid may be utilized.

The passage of products of the formula III to products of the formula III and of the products V to the products of the formula V (where R is alkyl) is made with the aid of a diazoalkane having 1 to 4 carbon atoms, such as diazomethane, diazoethane or diazobutane.

The saponification agent employed in the passage of products of formula IV to products of formula V is an alkaline base, preferably an aqueous alkali metal hydroxide solution such as sodium or potassium hydroxide.

The decarboxylation of the carboxyl group of the cyclopentanic ring of product V is realized by thermal decarboxylation. The temperature employed is between 120° C and 200° C, preferably about 140° C. This can be controlled by operating in an organic solvent boiling at the desired temperature such as xylene.

The oxidizing agent capable of oxidizing a hydroxyl group to a ketone group which is reacted on the mixture of products VI and VI' or on one of its constituents is preferably silver silicate in the presence of an inert organic solvent at temperatures up to the reflux temperature. However other oxidizing agents such as chromic acid anhydride in acetonic solution, manganese bioxide or the chromic acid anhydride-pyridine complex may be employed.

The transformation of the mixture of products of formulaes VII and VII' or of each of its constituents into the products of formula I is effected by the aid of ketonic alkylating organo-magnesium derivatives of the formula R' MgX where R' has the above-assigned values and X is a halogen preferably selected from the group of chlorine, bromine and iodine. The reaction is advantageously effected in an organic solvent such as ethyl ether or tetrahydrofuran.

The acid which is utilized at the end of the process to hydrolyze the alkoxy group attached to the cyclopentanic ring to the ketonic group is preferably aqueous hydrochloric acid. However any aqueous organic or inorganic acid capable of converting an enol to a ketone can be employed such as aqueous sulfuric acid or an organic acid such as formic acid or oxalic acid in an aqueous media.

A variant in the process for the preparation of products of formula I in which the radical R' represents an acetylenic group having the formula

R''—C≡C— in which R'' is hydrogen or alkyl having 1 to 2 carbon atoms, is likewise part of the invention. In this variant, the above process is followed to the production of the mixture of products of the formulaes VII and VII', or one or the other of them. Thereafter the product VII or the product VII' or the mixture, as desired, is reacted with an alkylating derivative having the formula

R''—C≡C—M wherein M represents an alkali metal and R'' has the above-assigned values, in liquid ammonia or in an inert organic solvent. A mixture of products of formula I in which A represents alkoxy and R' represents the R''—C≡C— radical are obtained which can be transformed, if desired, into other products of formula I in which R' represents the R''—C≡C— radical according to the processes described above. The alkali metal M can be lithium, sodium or potassium. The inert organic solvent can be, for example, benzene or toluene.

The constituents of the mixtures formed by the products of formulaes VI and VI', VII and VII' and the different products of formula I can be separated by the usual physical methods, in particular by chromatography.

The salification of the products of formula I in which R represents hydrogen can be realized by the usual methods. The salts can be obtained for example, by the action of a mineral base, such as an alkali metal hydroxide such as sodium or potassium hydroxide or an organic amine base such as triethylamine, on the products of formula I where R=H. The salification is conducted preferably in a solvent or a mixture of solvents particularly water, ethyl ether, ethanol or acetone.

In another variant of the process, compounds of the formula

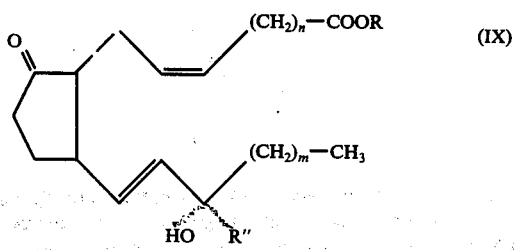

(IX)

wherein R, n and m have the above definition and R'' is alkenyl of 2 to 4 carbon atoms with each carbon atom of the double bond having at least one hydrogen attached thereto may be prepared by subjecting a compound of the formula

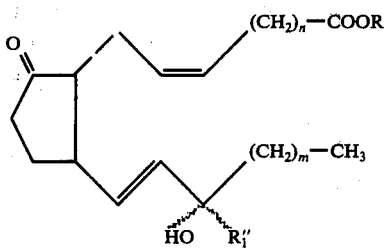

wherein $R_1''$ is alkynyl of 2 to 4 carbon atoms to hydrogenation in the presence of a hydrogenation catalyst.

Examples of suitable groups for $R_1''$ are ethynyl, 1-propynyl, 2-propynyl, 1-butynyl, 2-butynyl, 3-butynyl and 1-methyl-2-propynyl which result in R'' being vinyl, 1-propenyl, 2-propenyl, 1-butenyl, 2-butenyl, 3-butenyl and 1-methyl-2-propenyl, respectively. Particularly preferred as the starting material is the compound of formula X wherein R is methyl, n is 3, m is 4 and $R_1''$ is ethynyl which results in the product of formula IX wherein R'' is vinyl.

The catalyst for the hydrogenation is preferably palladized barium sulfate used in the presence of a trace of quinoline but also useful are palladized calcium carbonate in the presence of lead acetate, palladized carbon black in the presence of pyridine or Raney nickel.

This process is particularly adapted for obtaining the compounds of formula IX in the form of their individual isomers since the compounds of formula I with a triple bond are more readily separated from their isomeric mixtures.

In addition, the process of the invention enables the obtention of novel industrial products useful for the preparation of products of formula I. Collectively these intermediates are products of the formula VIII

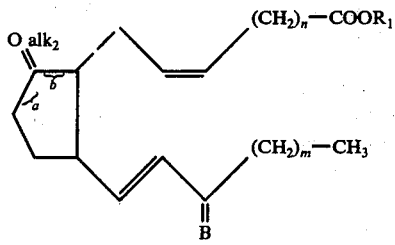

wherein $R_1$ represents hydrogen or alkyl having 1 to 4 carbon atoms, m is a whole number equal to 3,4 or 5, n is a whole number equal to 2,3 or 4, $alk_2$ is alkyl having 1 to 4 carbon atoms, one of a or b represents a double bond and B is oxygen

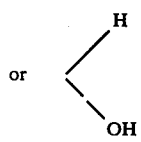

The products of formula II utilized as starting materials in the process of the invention are described together with the process of obtaining them, in the French Pat. No. 2,085,654 as well as U.S. Pat. application Ser. No. 138,276, filed Apr. 28, 1971.

The products of formula I and their salts when R = H, can exist in both racemic and optically active forms.

The optically active isomers can be separated by the customarily employed methods. For example either the starting, intermediate or final racemic acids can be resolved by the aid of salts formed with optically active bases.

The following examples are illustrating of the practice of the invention without being limitative in any respect.

EXAMPLE 1

Methyl (8RS, 12RS, 15SR)-(5Z, 13E)-15-ethynyl-15-hydroxy-9-oxo-5,13-prostadienoate and methyl (8RS, 12RS, 15RS)-(5Z, 13E)-15-ethynyl 15-hydroxy 9-oxo 5,13-prostadienoate Step A: Ethyl (8RS, 12RS, 15SR)-(5Z, 13E)-10-carbethoxy-15-hydroxy-9-oxo-5,13-prostadienoate 243 mg of ethyl (8RS, 12RS, 15SR)-(5Z, 13E)-10-carbethoxy-9-oxo-15-tetrahydropyranyloxy-5,13-prostadienoate (Example VI, Step B, S.N. 138,276, filed April 28, 1971) were introduced into a mixture of 4 cc of an aqueous solution containing 2 parts per thousand of oxalic acid and 4 cc of ethanol. The mixture was heated to 48° C for eight hours, then evaporated to dryness under vacuum. The residue was extracted with ether. The etheral phase was washed with water and dried over magnesium sulfate. After evaporation of the ether, the oil obtained was subjected to chromatography through silica gel with the aid of a 1:1 mixture of cyclohexane and ethyl acetate. 93 mg of ethyl (8RS, 12RS, 15SR)-(5Z, 13E)-10-carbethoxy-15-hydroxy-9-oxo-5,13-prostadienoate were thus obtained in the form of yellow oil.

Analysis: ($C_{25}H_{40}O_6$)

| | | |
|---|---|---|
| Calculated: | 68.80% C | 9.24% H |
| Found: | 68.5% | 9.2% |

Step B: Ethyl (8RS, 12RS, 15SR)-(5Z, 9, 13E)-10-carbethoxy-15-hydroxy-9-methoxy-5,9,13-prostatrienoate (VIII)

550 mg of the product prepared according to the preceding step were dissolved in 4 cc of methylene chloride. The solution was cooled to 0° C and 15 cc of a solution containing 15 gm/l of diazomethane in methylene chloride were added. The temperature of the reaction mixture was allowed to rise to room temperature and the reaction continued for five hours. Diazomethane in excess was then evaporated and thereafter the methylene chloride was evaporated under vacuum. 564 mg of ethyl (8RS, 12RS, 15SR)-(5Z, 9, 13E)-10-carbethoxy-15-hydroxy-9-methoxy-5,9,13-prostatrienoate were thus obtained in the form of a pale yellow oil.

U.V. Spectra (ethanol)
λMax. = 254 mm ε = 9,800
I.R. Spectra (chloroform)
1631 cm$^{-1}$ C≡C
1697 cm$^{-1}$ C=O conjugated
1733 cm$^{-1}$ C=O non-conjugated
3605 cm$^{-1}$ OH Step C: (8RS, 12RS, 15SR)-(5Z, 9, 13E)-10-carboxy-15-hydroxy-9-methoxy-5,9,13-prostatrienoic acid 216 gm of the product according to the preceding step were dissolved in 21 cc of ethanol. 14.4 cc of normal aqueous sodium hydroxide were added and the mixture was heated to 70° C for six hours. Thereafter, 4.8 cc of normal aqueous sodium hydroxide were again added and the mixture was heated to 70° C for a further ten hours. Next the ethanol was evaporated and the residue was taken up in a mixture of water and ether. The aqueous phase which separated was acidified by 2N hydroxhloric acid solution, then saturated with sodium chloride. The mixture was extracted with ether. The ethereal phase was dried over magnesium sulfate and concentrated under vacuum. 1.89 gm of (8RS, 12RS, 15SR)-(5Z, 9, 13E)-10-carboxy-15-hydroxy-9-methoxy-5,9,13-prostatrienoic acid were thus obtained in the form a thick yellow oil.

I.R. Spectra (chloroform)
1626 cm$^{-1}$ C=C
1710 cm$^{-1}$ C=O large band
3501 cm$^{-1}$ OH Step D: Methyl (8RS, 12RS, 15SR)-(5Z, 9, 13E)-15-hydroxy-9-methoxy-5,9,13-prostratrienoate and methyl (12RS, 15SR)-(5Z, 8, 13E)-15-hydroxy-9-methoxy-5,8,13-prostrienoate 2.35 gm of the diacid prepared according to the preceding step were introduced into 185 cc of xylene. The mixture was heated to reflux for eight hours; then the xylene was evaporated under vacuum. The thick oil obtained was dissolved in 10 cc of methylene chloride. The solution was cooled to 0° C and 30 cc of a solution containing 15 gm/l of diazomethane in methylene chloride were slowly added. After termination of the addition the excess diazomethane was evaporated and the methylene chloride was evaporated under vacuum. A yellow oil was obtained which was filtered through silica and eluted with an 8:2 mixture of benzene and ethyl acetate. 1.95 gm of oil were obtained which was shown by MNR spectography to be a mixture of methyl (8RS, 12RS, 15SR)-(5Z, 9, 13E)-15-hydroxy-9-methoxy-5,9,13-prostatrienoate and methyl (12RS, 15SR)-(5Z, 8, 13E)-15-hydroxy-9-methoxy-5,8,13-prostatrienoate in the approximate proportion of 3/5 to 2/5.

MNR Spectra (deuterochloroform)
Peak of 9-methoxy-$\Delta^9$ at 216.5 Hz
Peak of 9-methoxy-$\Delta^8$ at 217.5 Hz Step E: Methyl (8RS, 12RS)-(5Z, 9, 13E)-9-methoxy-15-oxo-5,9,13-prostatrienoate and methyl (12RS)-(5Z, 8, 13E)-9-methoxy-15-oxo-5,8.13-prostatrienoate 180 mg of the mixture obtained in the preceding step were introduced into 13 cc of benzene. 580 mg of silver silicate were added and the mixture was heated to reflux for 3½ hours. After cooling, the mixture was filtered and the filter cake was washed with benzene. The filtrate was evaporated under vacuum giving 160 mg of an oil which was shown by MNR spectography to be a mixture of methyl (8RS, 12RS)-(5Z, 9, 13E)-9-methoxy-15-oxo-5,9,13-prostatrienoate and methyl (12RS)-(5Z, 8, 13E)-9-methoxy-15-oxo-5,8,13-prostatrienoate in the approximate proportion of 4/5 to 1/5.

MNR Spectra (deuterochloroform)
Peak of 9-methoxy-$\Delta^9$ at 214.5 Hz
Peak of 9-methoxy-$\Delta^3$ at 216.5 Hz Step F: Methyl (8RS, 12RS, 15$\xi$)-(5Z, 9, 13E)-15-ethynyl-15-hydroxy-9-methoxy-5,9,13-prostatrienoate and methyl (12RS, 15$\xi$)-(5Z, 8, 13E)-15-ethynyl-15-hydroxy-9-methoxy-5,8,13-prostatrienoate 500 mg of the mixture obtained in the preceding step were dissolved in 3 cc of tetrahydrofuran. 3.6 cc of a 0.5 N solution of ethynyl magnesium bromide in tetrahydrofuran were added. The mixture was agitated for one hour at room temperature; then again 1.4 cc of the magnesium Grignard solution were added. The mixture was agitated for a further 1½ hours at room temperature. This reaction mixture was poured into a saturated aqueous iced solution of ammonium chloride. The mixture was extracted with ether. After washing and drying the organic phase, it was evaporated under vacuum and an oil was obtained. The oil was purified by filtration through silica gel in a 95:5 mixture of benzene and ethyl acetate. This gave 1.39 mg of a mixture of methyl (8RS, 12RS, 15$\xi$)-(5Z, 9, 13E)-15-ethynyl-15-hydroxy-9-methoxy-5,9,13-prostatrienoate and methyl (12RS, 15$\xi$)-(5Z, 8, 13E)-15-ethynyl-15-hydroxy-9-methoxy-5,8,13-prostatrienoate.

MNR Spectra (deuterochloroform)
Peak of 9-methoxy-$\Delta^9$ at 214.5 Hz
Peak of 9-methoxy-$\Delta^8$ at 217 Hz Step G: Methyl (8RS, 12RS, 15SR)-(5Z, 13E)-15-ethynyl-15-hydroxy-9-oxo-5,13-prostadienoate and methyl (8RS, 12RS, 15RS)-(5Z, 13E)-15-ethynyl-15-hydroxy-9-oxo-5,13-prostadienoate 139 mg of the mixture obtained in the preceding step were dissolved in 5 cc of ethanol. 5 cc of a 1:1 mixture of 0.1 N aqueous hydrochloric acid and ethanol were added. The mixture was allowed to stand for 45 minutes. Then the ethanol was evaporated under vacuum. The residue was taken up in ether. The ethereal phase was washed with aqueous sodium chloride, then dried over magnesium sulfate. After evaporation of the ether, a yellow oil was obtained which was subjected to chromatography through silica gel with the aid of 8:2 mixture of benzene and ethyl acetate. 38 mg of methyl (8RS, 12RS, 15RS)-(5Z, 13E)-15-ethynyl-15-hydroxy-9-oxo-5,13-prostadienoate and 24 mg of methyl (8RS, 12RS, 15SR)-(5Z, 13E)-15-ethynyl-15-hydroxy-9-oxo-5,13-prostadienoate were separated. The first product had, in thin layer chromatography in the system of 8 parts benzene and 2 parts ethylacetate, an Rf of 0.34; the second product had an Rf of 0.28.

IR Spectra (chloroform)
Practically identical for the two products.
3588 cm$^{-1}$ OH
3303 cm$^{-1}$ —C≡CH
1739 cm$^{-1}$ CO

EXAMPLE 2

Methyl-(8RS, 12RS, 15$\xi$)-(5Z, 13E)-15-hydroxy-15-methyl-9-oxo-5,13-prostadienoate Operating according to Steps F and G of Example 1, starting from the mixture of methyl (8RS, 12RS)-(5Z, 9, 13E)-9-methoxy-15-oxo-5,9,13-prostatrienoate and methyl (12RS)-(5Z, 8, 13E)-9-methoxy-15-oxo-5,8,13-prostatrienoate, but by utilizing methyl magnesium iodide, a yellow oil was obtained which is methyl (8RS, 12RS, 15$\xi$)-(5Z, 13E)-15-hydroxy-15-methyl-9-oxo-5,13-prostadienoate.

Thin layer chromatography in the system of 9 parts of cyclohexane and 1 part ethyl acetate gave a Rf of 0.5.
IR Spectra (chloroform)
3595 cm$^{-1}$:OH
1735 cm$^{-1}$:CO
MNR Spectra (deuterochloroform)
Peak at 140 Hz:OH in the 15 position
Peak at 77.5 Hz:CH$_3$ in the 15 position.

EXAMPLE 3

Methyl (8RS, 12RS, 15ξ)-(5Z, 13E)-15-hydroxy-9-oxo-15-vinyl-5,13-prostadienoate

By operating according to Steps F and G of Example 1, starting from the mixture of methyl (8RS, 12RS)-(5Z, 9, 13E)-9-methoxy-15-oxo-5,9,13-prostatrienoate and methyl (12RS)-(5Z, 8, 13E)-9-methoxy-15-oxo-5,8,13-prostatrienoate, but while utilizing vinyl magnesium bromide, a yellow oil was obtained which was methyl (8RS, 12RS, 15ξ)-(5Z, 13E)-15-hydroxy-9-oxo-15-vinyl-5,13-prostadienoate.

Thin layer chromatography in the system of 9 parts benzene and 1 part ethyl acetate gave a Rf of 0.2.
MNR Spectra (deuterochloroform)
Peak at 146 Hz:OH in the 15 position
Triplet at 451.5, 461.5 and 479 Hz:H$_2$ of the vinyl group
Quadruplet at 517, 528, 535.5 and 546.5 Hz:H of the vinyl group.

EXAMPLE 4

Methyl (8RS, 12RS, 15SR)-(5Z, 13E)-15-hydroxy-9-oxo-15-vinyl 5,13-prostadienoate A mixture of 108 g of methyl (8RS, 12RS, 15SR)-(5Z, 13E)-15-ethynyl-15-hydroxy-9-oxo-5,13-prostadienoate, 10 ml of ethyl acetate, 20mg of 5.25% palladium or barium sulfate and 0.1 ml of quinoline was cooled to 0° C and stirred in a hydrogen atmosphere for 15 minutes during which 6.5 ml of hydrogen were absorbed. The catalyst was removed by filtration and the filtrate was washed with an iced solution of N hydrochloric acid and then with water, dried over magnesium sulfate and evaporated to dryness under reduced pressure. The residue was chromatographed over silica gel and elution with a 9-1 benzene-ethyl acetate mixture yielded 60 mg of methyl (8RS, 12RS, 15SR)-(5Z, 13E)-15-hydroxy-15-vinyl-9-oxo-5,13-prostadienoate in the form of a clear yellow oil.

Thin-layer chromatography with silica and a 9-1 benzene-ethyl acetate eluant showed an RF 0.2.
RMN Spectra (deuterochloroform):
H of hydroxyl in the 15-position: 146 Hz
H of vinyl in 15-position: quadruplet 517, 528, 535.5 and 546.5 Hz
H$_2$ of vinyl in 15-position: triplet 451.5, 461.5 and 479 Hz

EXAMPLE 5

Methyl (8RS, 12RS, 15RS)-(5Z, 13E)-15-hydroxy-15-vinyl-9-oxo-5,13-prostadienoate A mixture of 108 mg of methyl (8RS, 12RS, 15RS)-(5Z, 13E)-15-ethynyl-15-hydroxy-9-oxo-5,13-prostadienoate, 10 ml of ethyl acetate and 20 mg of 5.25% palladized barium sulfate was stirred in a hydrogen atmosphere for 7 minutes during which 6.5 ml of hydrogen were absorbed and the catalyst was removed by filtration. The filtrate was washed with an iced N hydrochloric acid solution and then with water, dried over magnesium sulfate and evaporated to dryness under reduced pressure. The residue was chromatographed over silica gel and elution with a 9-1 benzeneethyl acetate mixture yielded 40 mg of methyl (8RS, 12RS, 15RS)-(5Z, 13E)-15-hydroxy-15-vinyl-9-oxo-5,13-prostadienoate in the form of a clear yellow oil.

Thin-layer chromatography with silica and a 9-1 benzeneethyl acetate eluant gave a Rf = 0.2.
RMN Spectra (deuterochloroform):
H of hydroxyl in 15-position: 145 Hz
H of vinyl in 15-position: quadruplet 521, 531, 538.5 and 549.5 Hz
H of vinyl in 15-position: triplet 453, 463.5 and 481 Hz.

PHARMACOLOGICAL DATA

Hereafter in this study, methyl (8RS, 12RS, 15SR)-(5Z, 13E)-15-ethynyl-15-hydroxy-9-oxo-5,13-prostadienoate will be designated product A; methyl (8RS, 12RS, 15RS)-(5Z, 13E)-15-ethynyl-15-hydroxy-9-oxo-5,13-prostadienoate will be designated product B, and methyl (8RS, 12RS, 15ξ)-(5Z, 13E)-15-hydroxy-15-methyl-9-oxo-5,13-prostadienoate will be designated product C.

1. Hypotensive Activity

The products were utilized in solution in physiological serum containing 10% of ethanol. These solutions were administered intravenously to rabbits anesthetized with urethane and the carotidien pressure was measured. The dosage which lowered this pressure 30% was found to be equal to 20 µg/kg of product A, 50 µg/kg of product B and 2 µg/kg of product C. The return to the normal arterial pressure occurred in 3 to 5 minutes.

At a dose of 50 µg/kg, product A provoked a maximum fall of the carotidien pressure attaining an average of 60%. It was followed by a residual hypotension of 10 to 30% which leasted more than 30 minutes.

In the same conditions, prostaglandine A$_2$, (8RS, 12RS, 15SR)-(5Z, 10, 13E)-15-hydroxy-9-oxo-5,10,13-prostatrienic acid caused a fall of carotidien pressure of 30% at a dose of 5 µg/kg and caused a fall of pressure of 50% at a dose of 50 µg/kg with a return to normal pressure in about 5 minutes.

2. Contracture Activity on the Guinea Pig Isolated Ileum

This test is effected on the isolated ileum of the guinea pig in a trough containing 10 cc of Tyrode liquid and under constant oxygenation. The test determined the concentration of the test product provoking a contraction of the organ comparable to that provoked by 10ng/cc of acetylcholine Under the experimental conditions, the average contracturing dose was 0.005 µg/ml for product A, 0.1 µg/ml of product B and 0.02 µg/ml for product C.

3. Antibronchoconstrictive Activity a. Against histamine in anesthetized guinea pigs The technique of the "overflow" of the lungs was used in order to measure this activity as described by Konzett et al, Arc. Expl. Path. Pharmacol. (1940) 195, 71. The test was conducted on male guinea pigs weighing from 200 to 500 gm and anesthetized with urethane. The animals were subjected to artifical respiration and the pressure of the air not flowing into the lungs was measured.

The test consisted in registering the increase of pressure induced by histamine administered intravenously at a dose of 10 μg/kg and the inhibition of this effect by the previous injection of the product studied. In these conditions, product A was active at a dose of 100 μg/kg, administered intravenously, and product C was active starting from the dose of 20 μg/kg.

b. Against a bronchoconstrictor aerosol in conscious guinea pigs

The bronchoconstrictor utilized was either histamine dihydrochloride (at a concentration of 0.4%) or acetylcholine hydrochloride (at a concentration of 2%). The guinea pigs were subjected to a first aerosol spraying which allowed the determination of the average time of resistance. Four hours later, they underwent a second aerosol spraying, one minute after an intravenous injection of product A at a dose of 500 μg/kg.

The results are given in the following Table.

TABLE

|  | Number of Guinea Pigs | Guinea Pigs Whose Time of Resistance Has At Least Doubled | Time of Resistance in Seconds | | Percent of Increase Corrected for the Time of Resistance |
|---|---|---|---|---|---|
|  |  |  | Before Treatment | After Treatment |  |
| Histamine Controls | 5 | 0 | 74 ± 7 | 71 ± 15 (−4%) |  |
| Treated by Product A | 5 | 4 | 82 ± 4 | 183 ± 37 (+123%) | 127 |
| Acetylcholine Controls | 7 | 0 | 56 ± 5 | 62 ± 9 (+10%) |  |
| Treated by Product A | 7 | 3 | 56 ± 5 | 137 ± 38 (+145%) | 135 |

The preceding specific embodiments are illustrative of the practice of the invention. It is to be understood, however, that other expedients known to those skilled in the art, or disclosed herein, may be followed without departing from the spirit of the invention or the scope of the appended claims.

We claim:

1. A compound of the formula

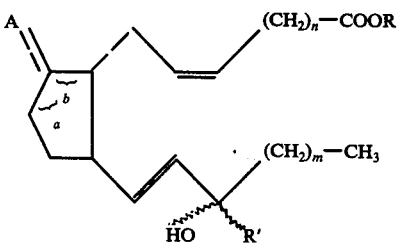

wherein R is a member selected from the group consisting of H, lower alkyl having 1 to 4 carbon atoms and acid salts of pharmaceutically compatible bases, m is an integer 3,4 or 5, n is an integer 2,3 or 4, R' is a member selected from the group consisting of alkenyl of 2 to 4 carbon atoms and cycloalkenyl of 3 to 6 carbon atoms, A is a member selected from the group consisting of ketonic oxygen and alkoxy of 1 to 4 carbon atoms, one of a or b being double bond when A is alkoxy, the dotted line to A being a double bond when A is a ketonic oxygen, and the wavy lines represent a paired configuration selected from the group consisting of α,β and β,α and mixtures thereof.

2. The compound of claim 1 wherein the compound is the 15RS or 15SR isomer of methyl (8RS, 12RS, 15ξ)-(5Z, 13E) 15-hydroxy-9-oxo-15-vinyl-5,13-prostadienoate or mixtures thereof.

3. The 15SR and 15RS isomers of methyl (8RS, 12RS, 15ξ)-(5Z, 13E)-15-hydroxy-9-oxo-15-vinyl-5,13-prostadienoate.

4. An antibronchoconstrictive composition comprising an effective amount of at least one compound of the formula

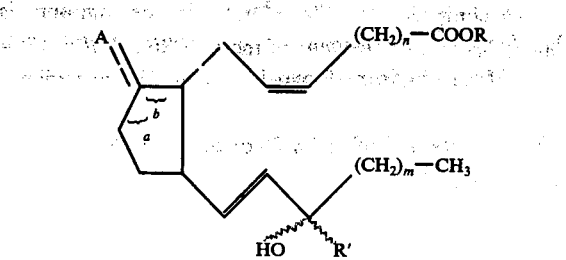

wherein R is a member selected from the group consisting of H, lower alkyl having 1 to 4 carbon atoms and acid salts of pharmaceutically compatible bases, m is an integer 3,4 or 5, n is an integer 2,3 or 4, R' is a member selected from the group consisting of alkenyl of 2 to 4 carbon atoms and cycloalkenyl of 3 to 6 carbon atoms, A is a member selected from the group consisting of ketonic oxygen and alkoxy of 1 to 4 carbon atoms, one of a or b being a double bond when A is alkoxy, the dotted line to A being a double bond when A is a ketonic oxygen, and the wavy lines represent a paired configuration selected from the group consisting of α,β and β,α and mixture thereof and a major amount of a pharmaceutical carrier.

5. The composition of claim 4 wherein the active compound is methyl (8RS, 12RS, 15RS)-(5Z, 13E)-15-hydroxy-9-oxo-15-vinyl-5,13-prostadienoate.

6. The composition of claim 4 wherein the active compound is methyl (8RS, 12RS, 15SR)-(5Z, 13E)-15-hydroxy-9-oxo-15-vinyl-5,13-prostadienoate.

7. An hypotensive composition comprising an hypotensively effective amount of at least one compound of the formula

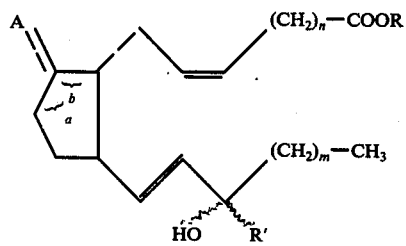

wherein R is a member selected from the group consisting of H, lower alkyl having 1 to 4 carbon atoms and acid salts of pharmaceutically compatible bases, $m$ is an integer 3,4 or 5, $n$ is an integer 2,3 or 4, R' is a member selected from the group consisting of alkenyl of 2 to 4 carbon atoms and cycloalkenyl of 3 to 6 carbon atoms, A is a member selected from the group consisting of ketonic oxygen and alkoxy of 1 to 4

8. A composition of claim 7 wherein the compound is the 15RS or 15SR isomer of methyl (8RS, 12RS, 15ξ)-(5Z, 13E) 15-hydroxy-9-oxo-15-vinyl-5,13-prostadienoate.

9. A compound of claim 20 of the formula

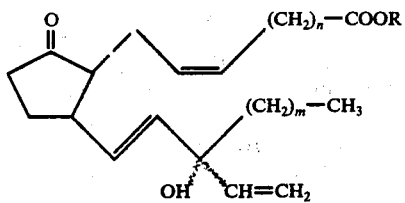

wherein R is hydrogen, lower alkyl of 1 to 4 carbon atoms or salts of pharmaceutically acceptable bases, $m$ is from 3 to 5 and $n$ is from 2 to 4.

* * * * *

UNITED STATES PATENT OFFICE
CERTIFICATE OF CORRECTION

Patent No. 4,061,729      Dated Dec. 6, 1977

Inventor(s) JACQUES MARTEL, JEAN BUENDIA and MICHEL VIVAT

It is certified that error appears in the above-identified patent and that said Letters Patent are hereby corrected as shown below:

| Col. | Line | | |
|---|---|---|---|
| 4 | 1-10 | | Formula should have Roman numeral "I" |
| 5 | 7-20 | | "(I)" should be --(I')-- |
| 11 | 40 | | formula should be --(VIII)-- |
| 12 | 36 | | "($C_{25}H_{40}O-_6$)" should be --($C_{25}H_{40}O_6$)-- |
| 12 | 40 | | "9, (VIII), 13E" should be --9, 13E-- |
| 14 | 49 | | "ethylacetate" should be ethyl acetate-- |
| 17 | 42-52 | Claim 1 |  should be 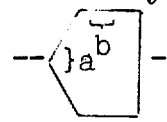 |
| 18 | 15 | Claim 4 | " " " " " " |
| 18 | 60 | Claim 7 | " " " " " " |

UNITED STATES PATENT OFFICE
CERTIFICATE OF CORRECTION

Patent No. 4,061,729          Dated December 6, 1977

Inventor(s) Jacques Martel, Jean Buendia and Michel Vivat

It is certified that error appears in the above-identified patent and that said Letters Patent are hereby corrected as shown below:

Column 19, line 7, after " 1 to 4" insert -- carbon atoms, one of a or b being a double bond when A is alkoxy, the dotted line to A being a double bond when A is a ketonic oxygen, and the wavy lines represent a paired configuration selected from the group consisting of $\alpha,\beta$ and $\beta,\gamma$ and mixtures thereof and a pharmaceutical carrier. --.

Column 19, line 14, "claim 20" should read -- claim 1 --.

Signed and Sealed this

Thirtieth Day of May 1978

[SEAL]

Attest:

RUTH C. MASON        LUTRELLE F. PARKER
Attesting Officer    Acting Commissioner of Patents and Trademarks